(12) United States Patent
Koyama et al.

(10) Patent No.: US 9,928,830 B2
(45) Date of Patent: Mar. 27, 2018

(54) INFORMATION PROCESSING APPARATUS AND INFORMATION PROCESSING METHOD

(71) Applicants: TERUMO KABUSHIKI KAISHA, Tokyo (JP); NEC CORPORATION, Tokyo (JP)

(72) Inventors: Miyuki Koyama, Kawasaki (JP); Tadashi Sameshima, Isehara (JP); Toshihide Tanaka, Tama (JP); Mayumi Ito, Tokyo (JP); Kazuyoshi Warita, Tokyo (JP); Masakazu Ishida, Tokyo (JP)

(73) Assignees: TERUMO KABUSHIKI KAISHA, Shibuya-Ku, Tokyo (JP); NEC CORPORATION, Minato-Ku, Tokyo (JP)

( * ) Notice: Subject to any disclaimer, the term of this patent is extended or adjusted under 35 U.S.C. 154(b) by 0 days.

(21) Appl. No.: 14/732,263

(22) PCT Filed: Oct. 23, 2013

(86) PCT No.: PCT/JP2013/006269
§ 371 (c)(1),
(2) Date: Jun. 5, 2015

(87) PCT Pub. No.: WO2014/087571
PCT Pub. Date: Jun. 12, 2014

(65) Prior Publication Data
US 2015/0371630 A1 Dec. 24, 2015

(30) Foreign Application Priority Data
Dec. 7, 2012 (JP) ................................ 2012-268101

(51) Int. Cl.
*G10L 17/00* (2013.01)
*G09B 21/00* (2006.01)
(Continued)

(52) U.S. Cl.
CPC ............ *G10L 15/063* (2013.01); *G09B 19/06* (2013.01); *G09B 21/00* (2013.01); *G10L 17/22* (2013.01); *G10L 25/48* (2013.01); *G10L 25/60* (2013.01)

(58) Field of Classification Search
USPC .... 704/249, 251, 270, 9, 260; 434/185, 156, 434/112; 381/104, 107, 57; 600/23
See application file for complete search history.

(56) References Cited

U.S. PATENT DOCUMENTS 4,507,750 A * 3/1985 Frantz ..................... G06F 17/28
704/251
4,749,353 A * 6/1988 Breedlove ............. G06F 17/273
434/169

(Continued)

FOREIGN PATENT DOCUMENTS

| JP | 2001249679 A | * | 9/2001 |
| JP | 2003-186379 A | | 7/2003 |

(Continued)

OTHER PUBLICATIONS

International Search Report (PCT/ISA/210) dated Jan. 14, 2014, by the Japanese Patent Office as the International Searching Authority for International Application No. PCT/JP2013/006269.

(Continued)

*Primary Examiner* — Neeraj Sharma
(74) *Attorney, Agent, or Firm* — Buchanan Ingersoll & Rooney PC

(57) ABSTRACT

An information processing apparatus and a method for performing speech training in speech rehabilitation are dis- (Continued)

closed. A report about content to be uttered in an utterance training is made to a trainee of the utterance training and the volume of a voice uttered by the trainee in response to the report is obtained. Then, the result of comparison between the obtained volume and a volume predetermined as a target volume is reported.

20 Claims, 12 Drawing Sheets

(51) Int. Cl.

| | | |
|---|---|---|
| *G10L 15/06* | (2013.01) | |
| *G10L 25/60* | (2013.01) | |
| *G09B 19/06* | (2006.01) | |
| *G10L 17/22* | (2013.01) | |
| *G10L 25/48* | (2013.01) | |
| *G06F 17/27* | (2006.01) | |
| *G10L 15/00* | (2013.01) | |
| *G10L 21/00* | (2013.01) | |
| *G09B 19/00* | (2006.01) | |
| *G09B 5/00* | (2006.01) | |
| *H03G 3/20* | (2006.01) | |
| *H03G 7/00* | (2006.01) | |

(56) References Cited

U.S. PATENT DOCUMENTS

| | | | | |
|---|---|---|---|---|
| 6,055,498 | A * | 4/2000 | Neumeyer | G09B 19/04 434/185 |
| 7,706,551 | B2 * | 4/2010 | Falcon | H04S 7/00 381/104 |
| 7,925,508 | B1 * | 4/2011 | Michaelis | G10L 17/26 600/300 |
| 7,962,342 | B1 * | 6/2011 | Coughlan | G10L 15/22 379/201.01 |
| 8,306,235 | B2 * | 11/2012 | Mahowald | H03G 3/32 381/104 |
| 2006/0069562 | A1 * | 3/2006 | Adams | G09B 5/00 704/251 |
| 2006/0204033 | A1 * | 9/2006 | Yoshimine | G09B 21/009 382/103 |
| 2006/0234193 | A1 * | 10/2006 | Sahashi | H04M 3/567 434/112 |
| 2008/0140412 | A1 * | 6/2008 | Millman | G09B 7/02 704/270 |
| 2009/0119109 | A1 | 5/2009 | Willmann et al. | |
| 2009/0197224 | A1 * | 8/2009 | Nariyama | G09B 5/04 434/156 |
| 2010/0299137 | A1 * | 11/2010 | Abe | G10L 25/48 704/9 |
| 2012/0130154 | A1 * | 5/2012 | Sajan | G10L 21/06 600/23 |

FOREIGN PATENT DOCUMENTS

| | | |
|---|---|---|
| JP | 2004-226556 A | 8/2004 |
| JP | 2004-252019 A | 9/2004 |
| JP | 2007-292979 A | 11/2007 |
| JP | 2008-298933 A | 12/2008 |
| JP | 2009-538441 A | 11/2009 |
| WO | WO 2013/168363 A1 | 11/2014 |
| WO | WO 2013/168364 A1 | 11/2014 |

OTHER PUBLICATIONS

Notification of Reasons for Refusal dated Jun. 20, 2017 in corresponding Japanese Patent Application No. 2014-550894, and an English translation thereof.

* cited by examiner

FIG. 3A

TEXT DATABASE 222

| IDENTIFICATION NUMBER (ID) | TRAINING TEXT ITEM | LEVEL | READ INFORMATION |
|---|---|---|---|
| 000001 | HA-RE | 1 | |
| 000002 | A-ME | 1 | |
| 000003 | WA-TA-SHI-WA, GAKKO-E, IKU | 2 | |
| 000004 | | | |
| ... | | | |
| 301 | 302 | 303 | 304 |

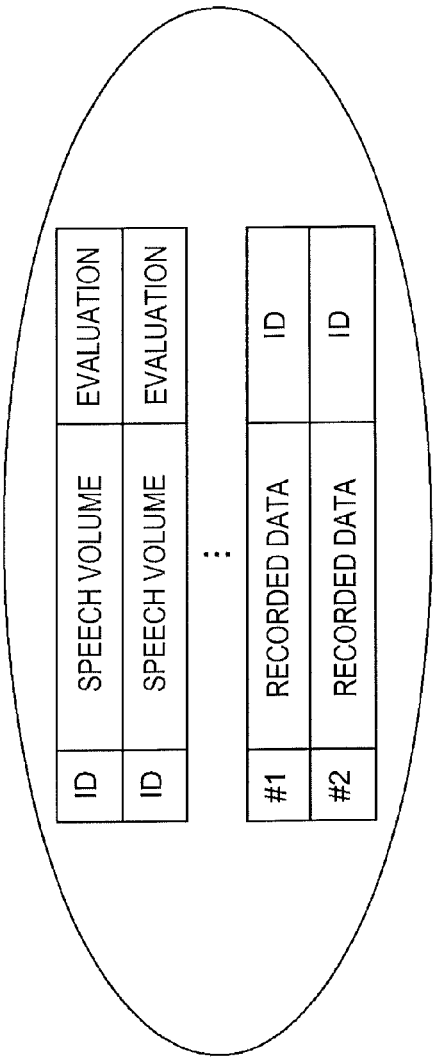

FIG. 8A

TRAINEE INFORMATION TABLE 223

| NAME | FACE RECOGNITION INFORMATION | AUTHENTI-CATION INFORMATION | EXERCISE SITUATION | LEVEL 1 | ... | LEVEL 5 |
|---|---|---|---|---|---|---|
| x x x | | | | | ... | |
| nnnn | | | | | ... | |
| ssss | | | | | ... | |
| ⋮ | | | | | | |

TRAINEE INFORMATION TABLE 223

| NAME | FACE RECOGNITION INFORMATION | AUTHENTI-CATION INFORMATION | EXERCISE SITUATION | WEAK SOUND |
|---|---|---|---|---|
| x x x | | | | |
| nnnn | | | | |
| ssss | | | | |
| ⋮ | | | | |

321  322  323  324  802

INFORMATION PROCESSING APPARATUS AND INFORMATION PROCESSING METHOD

CROSS-REFERENCES TO RELATED APPLICATIONS

This application is a continuation of International Application No. PCT/JP2013/006269 filed on Oct. 23, 2013, and claims priority to Japanese Application No. 2012-268101 filed on Dec. 7, 2012, the entire content of both of which is incorporated herein by reference.

TECHNICAL FIELD

The present disclosure generally relates to an information processing apparatus and an information processing method.

BACKGROUND DISCUSSION

Speech rehabilitation can be performed, under guidance or supervision of speech therapists, on patients with language deficits such as those suffering from aphasia that can occur because the language area is damaged by a cerebrovascular accident such as cerebral hemorrhage or cerebral infarction, those suffering from dysarthria or the like that can occur because an organ related to articulation becomes dysfunctional, and those suffering from speech deficits due to, for example, Parkinson's disease.

In speech rehabilitation of such patients with speech deficits, training (speech training) for causing such patients to speak in a loud voice is one important option.

For example, JP-A-2007-292979 discloses an exercise assistance apparatus for assisting recovery from aphasia.

The exercise assistance apparatus in JP-A-2007-292979 is not intended for speech training that causes patients with speech deficits to speak in a loud voice. Accordingly, even if such an apparatus is used, patients with language deficits cannot perform speech training with a loud voice without the speech therapist, thereby reducing the efficiency of the training.

SUMMARY

In accordance with an exemplary embodiment, an information processing apparatus and method for performing speech training in speech rehabilitation are disclosed, which can address the above problems.

An information processing apparatus is disclosed for utterance training in speech rehabilitation, which can include an utterance content reporting means for making a report about content to be uttered in the utterance training to a trainee of the utterance training, calculation means for calculating a volume of a voice uttered by the trainee in response to the report, and comparison result reporting means for reporting a result of comparison between the volume calculated by the calculation means and a volume predetermined as a target volume.

In accordance with an exemplary embodiment, a patient with language deficits can exercise appropriate speech training.

An information processing method performed by an information processing apparatus is disclosed for utterance training in speech rehabilitation, the method comprising: an utterance content reporting step of making a report about content to be uttered in the utterance training to a trainee of the utterance training; a calculation step of calculating a volume of a voice uttered by the trainee in response to the report; and a comparison result reporting step of reporting a result of comparison between the volume calculated by the calculation step and a volume predetermined as a target volume.

A non-transitory computer-readable recording medium with a program stored therein is disclosed which causes a computer to function as means of an information processing apparatus, the means of the computer-readable recording medium comprising: utterance content reporting means for making a report about content to be uttered in the utterance training to a trainee of the utterance training; calculation means for calculating a volume of a voice uttered by the trainee in response to the report; and comparison result reporting means for reporting a result of comparison between the volume calculated by the calculation means and a volume predetermined as a target volume.

Other features and advantages of the present invention will become obvious from the following descriptions with reference to attached drawings. In the attached drawings, the same or similar components are given the same reference characters.

BRIEF DESCRIPTION OF THE DRAWINGS

The attached drawings are included in the specification and a part thereof, indicate embodiments of the invention, and are used together with descriptions thereof to describe the principle of the invention.

FIG. 3A shows an example of the data structure of a text database and a trainee information table.

FIG. 3B shows an example of the data structure of the text database and the trainee information table.

FIG. 8A shows another example of the data structure of the trainee information table.

FIG. 8B shows another example of the data structure of the trainee information table.

DETAILED DESCRIPTION

Embodiments of the present disclosure will be described with reference to the drawings. Since the following embodiments are exemplary examples of the present disclosure, technically preferable limitations are imposed thereon, but the scope of the disclosure is not limited to these aspects unless descriptions to limit the invention are given in the following description.

First Embodiment

1. Appearance Structure of a Rehabilitation Robot

Figure 1:
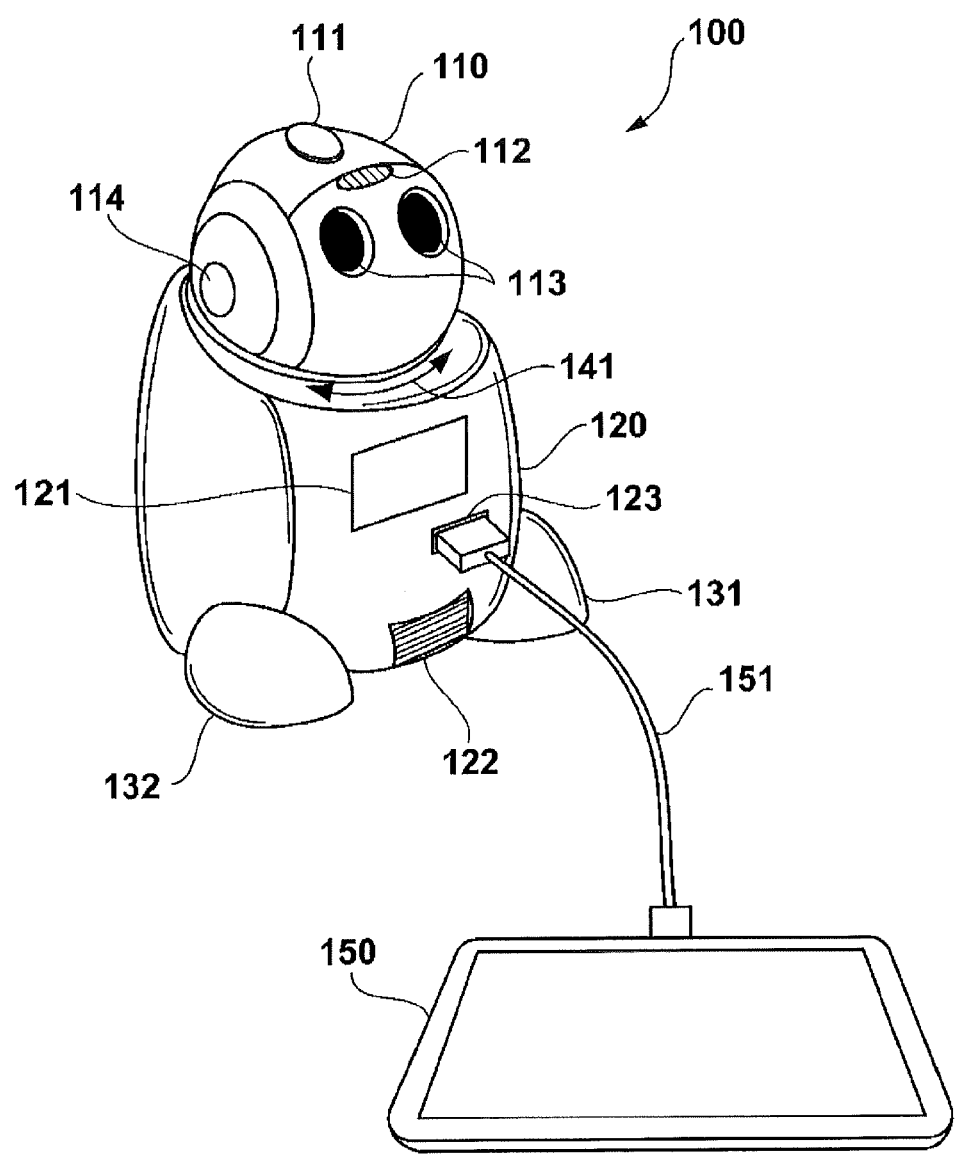
FIG. 1 shows the appearance structure of a rehabilitation robot including an information processing apparatus according to an embodiment of the present disclosure.

FIG. 1 shows the appearance structure of a rehabilitation robot 100, which is an information processing apparatus according to the present embodiment. As shown in FIG. 1, the rehabilitation robot 100 for assisting the speech exercise (speech training) by a trainee such as a patient with language deficits or the like can include a head 110, a body 120, and feet (a left foot 131 and a right foot 132).

The head 110 can include a switch 111 used by the user (speech therapist, trainee, or the like) of the apparatus to give various instructions to the rehabilitation robot 100, a camera 113 for imaging an external environment and grasping the position, the face orientation, and the like of the trainee, and a microphone 112 for obtaining a voice uttered by the trainee. In addition, the head 110 can include a lamp 114 illuminating or blinking according to an instruction by the switch 111 and a voice or the like input to the microphone 112.

The body 120 can include a touch panel display 121 for displaying data required for the rehabilitation of the trainee or for inputting various types of instructions through a touch operation and a speaker 122 for outputting a voice to the trainee. The touch panel display 121 may be built into the rehabilitation robot 100 or may be connected through an external output.

Since the body 120 has the left foot 131 and the right foot 132 connected thereto, the entire rehabilitation robot 100 can be moved in any direction. The head 110 is configured to rotate (for example, swing) in the direction of an arrow 141 relative to the body 120. Accordingly, the rehabilitation robot 100 can orient the entire body 120 toward the trainee or only the head 110 toward the trainee.

In addition, the body 120 has a connector unit 123 to which a cable 151 for connecting an external apparatus such as a tablet terminal 150 or the like can be connected. Since the function achieved by the touch panel display 121 is similar to that achieved by the tablet terminal 150 in the following embodiments, the touch panel display 121 may be omitted. In addition, connection with an external apparatus may be performed using wireless communication instead of a wired connection via the connector unit 123.

2. Functional Structure of the Rehabilitation Robot

Figure 2:
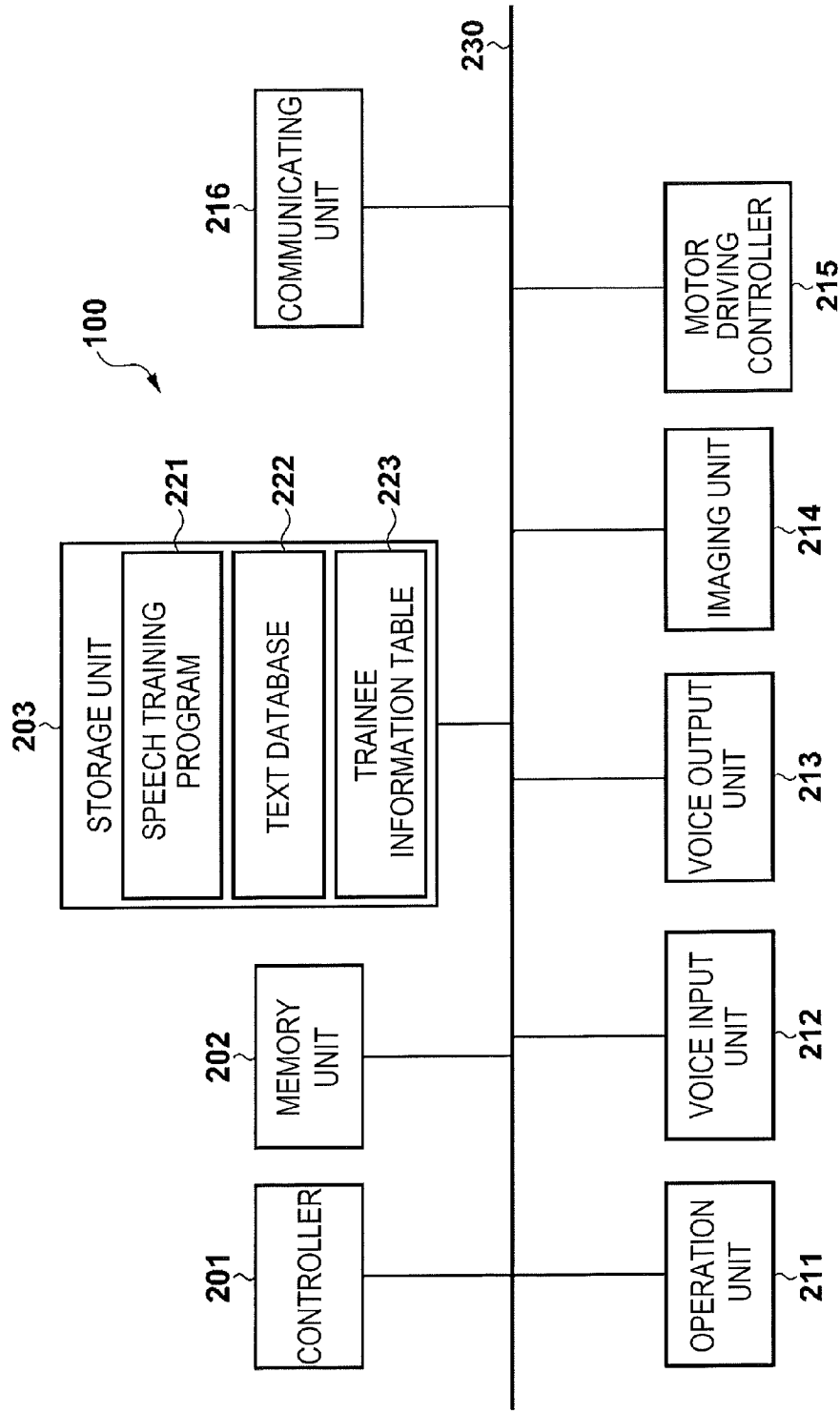
FIG. 2 is a block diagram showing an example of the functional structure of the rehabilitation robot.

Next, the functional structure of the rehabilitation robot 100 will be described. FIG. 2 shows the functional structure of the rehabilitation robot 100.

As shown in FIG. 2, the rehabilitation robot 100 can include a controller (computer) 201, a memory unit 202, and a storage unit 203. The storage unit 203 can function as storage means and can store a speech training program 221, a text database 222, and a trainee information table 223. The controller 201 achieves a speech training process, which will be described later, by executing the speech training program 221. The controller 201 performing the speech training program 221 is an example of a component achieving each of the means of the disclosure. A part of the function may be disposed in another apparatus such as a server or the like through a network.

The text database 222 can store words, word strings, and sentences used for speech training. In the following description of this specification, words, word strings, and sentences used for speech training are referred to as training text items. FIG. 3A shows an example of the data structure of the text database 222. As shown in FIG. 3A, each training text item can be assigned an identification number (ID) 301. A training text item 302 can register the data (referred to below simply as text data) of a training text item indicating a word, word string, or sentence. A level 303 can hold a training level determined by the mora number, the number of words, and the like of text data registered in the training text item 302. For example, the higher the mora number or the number of words, the higher the difficulty level of training becomes. Accordingly, such text data is given a higher training level. In accordance with an exemplary embodiment, for example, this example assumes training levels 1 to 5. Read information 304 can be used when a training text item is read out by a synthesized voice.

The trainee information table 223 registers information about trainees of speech training. FIG. 3B shows an example of the data structure of the trainee information table 223. A name 321 registers the name of a trainee. Face recognition information 322 can register information (such as a face feature quantity or the like) used by the controller 201 to recognize the face of a trainee. Authentication information 323 is information such as, for example, a password or the like used to authenticate a trainee. An exercise situation 324 records information about past speech training of the trainee such as the identification number (identification number of a training text item in the text database 222) of the training text item for which the trainee exercised speech training in the past, the measurement result of the speech volume for the training text item, the evaluation result, or the like. The exercise situation 324 records recording data including a predetermined number of past speeches. The speech therapist can know the exercise situation and the exercise achievement of a trainee with reference to the content recorded in the exercise situation 324.

Although the storage unit 203 stores various programs and data for achieving other functions of the rehabilitation robot 100, their descriptions are omitted. For example, the storage unit 203 can store computer programs and data used by the controller 201 to perform various processes, which will be described below, executed by the rehabilitation robot 100.

In FIG. 2, an operation unit 211 receives an operation input from a switch 111 or the touch panel display 121 and provides a signal indicating the operation for the controller 201, and controls the illumination of the lamp 114 and the display of the touch panel display 121 under the control of the controller 201. A voice input unit 212 stores a voice signal input from the microphone 112 in the memory unit 202 as voice data (digital data), under the control of the controller 201. A voice output unit 213 drives the speaker 122 and, for example, outputs a synthesized voice under the control of the controller 201. An imaging unit 214 controls the camera 113 and stores image information obtained by the camera 113 in the memory unit 202, under the control of the controller 201. A motor driving controller 215 controls motors for driving wheels disposed in the left foot 131 and the right foot 132 and controls a motor that is disposed in the head 110 and swings the head 110.

A communicating unit 216 can include the connector unit 123 and connects the controller 201 and the tablet terminal 150 so as to communicate with each other. Although the tablet terminal 150 and the rehabilitation robot 100 are interconnected via a wired manner in FIG. 1, it will be appreciated that the tablet terminal 150 and the rehabilitation robot 100 may be connected wirelessly. In accordance with an exemplary embodiment, the above components are interconnected via a bus 230. The text database 222 and the trainee information table 223 can be edited by the tablet terminal 150, a personal computer, and the like connected via the communicating unit 216.

3. Flow of a Speech Training Process

Figure 4:
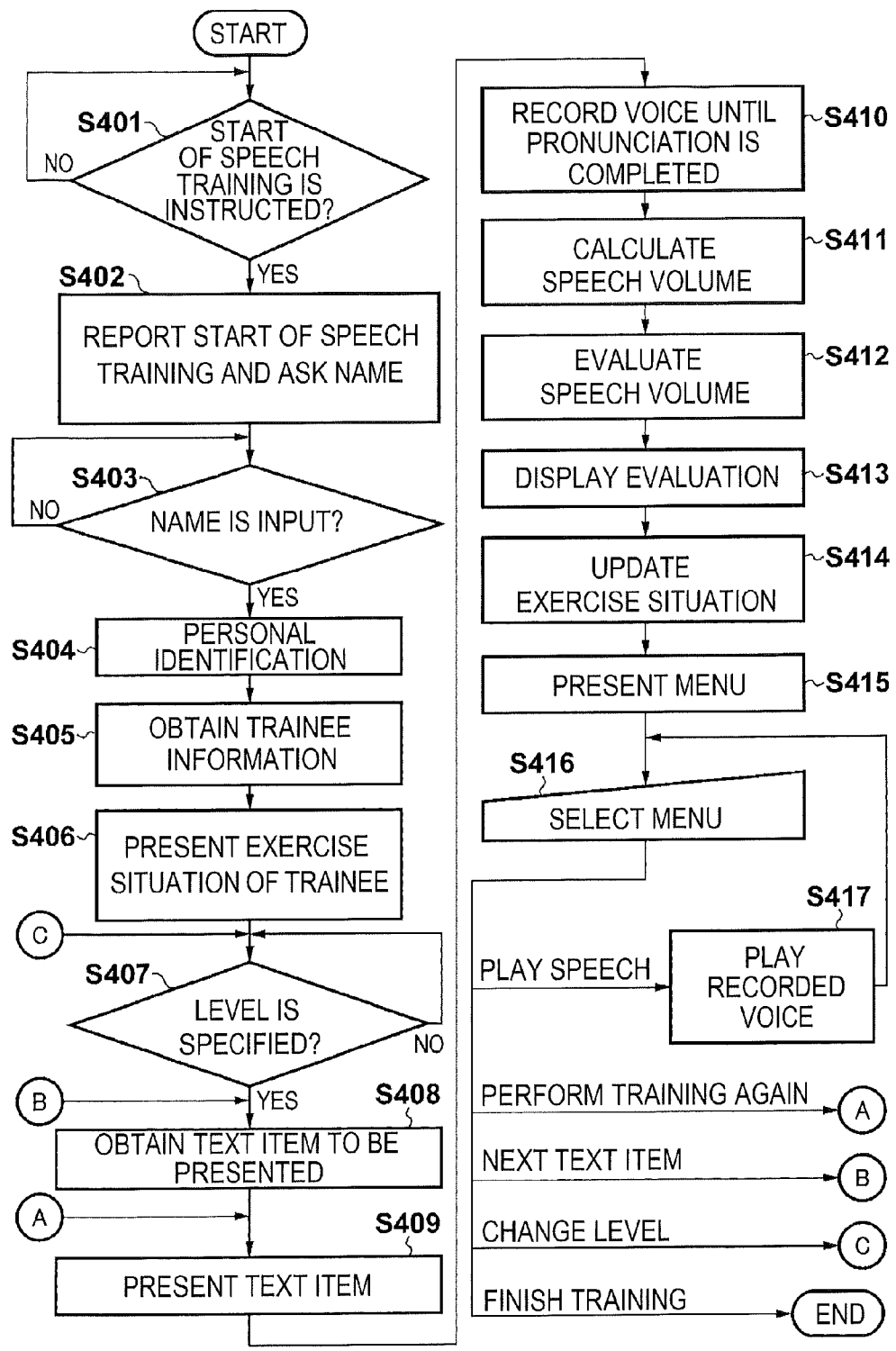
FIG. 4 is a flowchart showing a speech training process.

Next, a speech training process in the present embodiment performed when the controller 201 executes the speech training program 221 will be described with reference to the flowchart in FIG. 4. When the controller 201 detects a predetermined operation such as a depression of the switch 111 of the rehabilitation robot 100, a touch operation on the touch panel display 121, an operation through the tablet terminal 150, the processing proceeds to step S402 via step S401 and speech training is started. Since the user interface achieved by the touch panel display 121 is similar to that of the tablet terminal 150, the tablet terminal 150 is used in the following example. However, the user interface for the touch panel display 121 is provided by the controller 201, while the user interface for the tablet terminal 150 is achieved in cooperation between the CPU owned by the tablet terminal 150 and the controller 201. In addition, instead of an intelligent terminal such as the tablet terminal 150, a simple touch panel display may be connected. When such an external touch panel display is connected, the controller 201 performs the entire control as in the touch panel display 121.

In accordance with an exemplary embodiment, when speech training is started, the controller 201 notifies the trainee or speech therapist of the start of the speech training in step S402 and asks the name. For example, as shown in step S501 in FIG. 5, the controller 201 performs a synthesized voice output via the voice output unit 213. Alternatively, as shown in FIG. 6A, the tablet terminal 150 displays a speech training notification 601 and provides an interface (a software keyboard 602 and a text box 603) for inputting the name. Then, in step S403, the controller 201 waits for the name to be input by a voice via the microphone 112 or the name to be input from the tablet terminal 150.

When the controller 201 detects that the name is input by a voice (S502) or the name of the trainee is input from the tablet terminal 150, the processing proceeds to step S404 via step S403. The controller 201 verifies the personal identification of the trainee using the input name in step S404. In the present exemplary embodiment, such personal identification can be achieved by, for example, a face recognition process using the face recognition information 322 in the trainee information table 223 and the image taken by the camera 113. Personal identification may also be verified by accepting a password from the tablet terminal 150 and comparing it with the authentication information 323 or authentication may be performed using other types of biometric information (venous, fingerprint, or the like).

After verifying personal identification, the controller 201 obtains the trainee information (such as the name and exercise situation) of the person from the trainee information table 223 in step S405. Then, in step S406, the controller 201 presents the name and exercise situation of the person and asks the training level. For example, as shown in step S503 in FIG. 5, the controller 201 repeats the name of the trainee and asks the level applied in the last training and the level to be applied in this training, using a voice. Alternatively, as shown in FIG. 6B, the tablet terminal 150 asks the name (display 611) of the trainee, the level (display 612) of the last training, and the level (display 613) to be applied in this training. As the last training level, the highest level among the training text items registered as exercised in the exercise situation 324 may be presented. When personal identification fails, the controller 201 can report a mismatch between the name and the trainee using a voice output or display and the processing returns to step S401.

When the controller 201 detects that the training level is input by a voice as shown in step S504 or the training level is specified via the user interface provided by the tablet terminal 150 as shown in FIG. 6B, the processing proceeds to step S408 from step S407. The inputting of the training level via the user interface may be presented on the touch panel display 121 as well as on the tablet terminal 150 as an operation performed by the speech therapist. In step S408, the controller 201 obtains a training text item (text data) corresponding to a specified level from the text database 222. At this time, the controller 201 may also select a training text item with reference to the exercise situation 324. In this case, for example, the controller 201 may not select a training text item for which speech training has been exercised or may select a training text item with a low evaluation value.

In step S409, the controller 201 functions as utterance content reporting means for reporting content to be uttered in the utterance training to the trainee of utterance training. For example, the controller 201 presents the training text item obtained in step S408 to the trainee. The training text item may be presented by outputting it using a voice or displaying it on the tablet terminal 150. In the case of a voice output, the training text item is read out by a synthesized voice using the read information 304 and then output from the speaker 122 (step S505 in FIG. 5). In the case of display output, the training text item can be displayed on the tablet terminal 150 as shown in FIG. 6C.

Figure 7A:
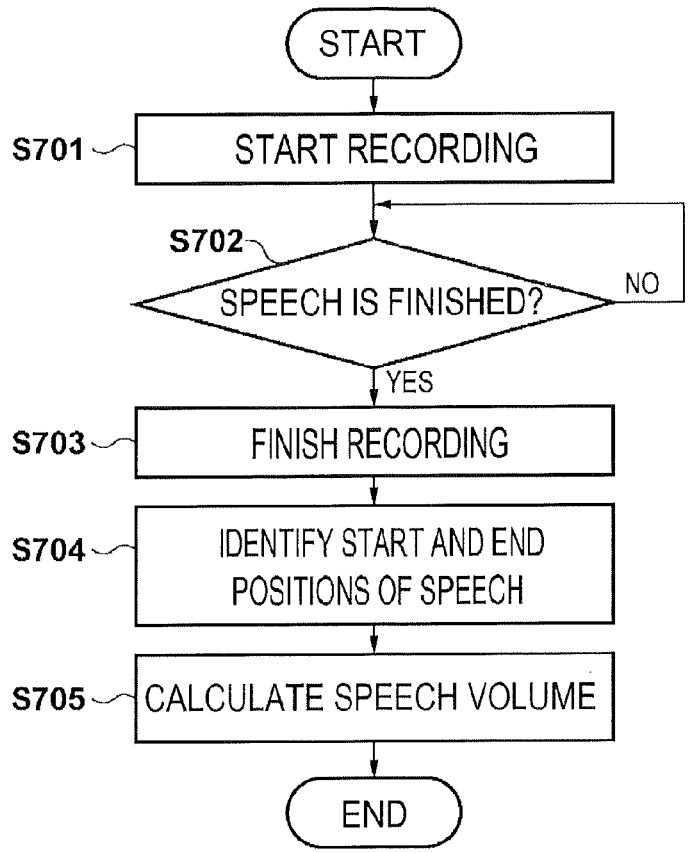
FIG. 7A shows the measurement process of a speech volume.

After presenting the training text item, the controller 201 starts recording with the microphone 112 in step S410 to record the speech (step S506 in FIG. 5) of the trainee. The recorded data is held in the memory unit 202. In step S411, the controller 201 calculates the speech volume by analyzing the recorded data. The recording of speech and the calculation of the speech volume in steps S410 and S411 will be described below with reference to the flowchart in FIG. 7A and an example of the voice input signal in FIG. 7B.

Figure 7B:
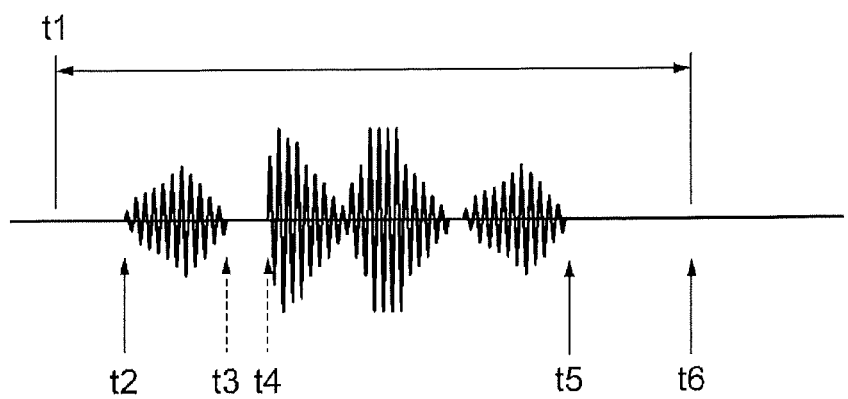
FIG. 7B shows the measurement process of the speech volume.

When the training text item is presented in step S409, the controller 201 starts storing (recording) the voice signal (actually, voice data to which A/D conversion and various preprocesses were applied) input from the microphone 112 in the memory unit 202 in step S701 by controlling the voice input unit 212 (time t1 in FIG. 7B). Until speech is determined to be completed in step S702, the controller 201 continues the recording started in step S701. In the present embodiment, when a period in which no voice input is present (a voiceless period) continues for a predetermined period of time (for example, 2 seconds) or greater, speech is determined to be completed. For example, in the case of the example shown in FIG. 7B, there is a voiceless period between time t3 and time t4. However, since the duration is shorter than the predetermined period of time, speech is not determined to be completed. In contrast, since it is determined that a voiceless state have continued after time t5 for the predetermined period of time at time t6, speech is determined to be completed at time t6.

In accordance with an exemplary embodiment, for example, a recording process is not limited to this processing and the controller 201 may trigger a recording process to start when a voice signal having a signal level (for example, volume) equal to or more than a predetermined level is input to the voice input unit 212 and may trigger a recording process to end when a voiceless period continues for a predetermined period or more. A voiceless period is not limited to a period in which no voice input is present strictly and may be a period in which the voice input unit 212 continuously detects a signal having a signal level (for example, volume) equal to or less than a predetermined level.

When speech is determined to be completed, the processing proceeds from step S702 to step S703. In step S703, the controller 201 finishes recording. Accordingly, when the voice signal is input as shown in FIG. 7B, recording is performed in the period from time t1 to time t6.

In step S704, the controller 201 identifies the start position and the end position of speech by analyzing the voice signal recorded in steps S701 to S703. In the present embodiment, the position at which a voice signal is first detected can be the start position of speech and the start position of a voiceless period that continues for a predetermined period of time can be the end position of speech. For example, in the example in FIG. 7B, time t2 is identified as the start position (start time) of speech and time t5 is identified as the end position (end time) of speech. In step S705, the controller 201 functions as calculation means for calculating the volume of a voice uttered by the trainee in response to a report. In accordance with an exemplary embodiment, for example, the controller 201 calculates the speech volume of the trainee based on a voice signal from the start position of speech to the end position of speech in the voice signal stored in the memory unit 202. Although various techniques can be applied to processing for calculating a volume based on a voice signal, for example, calculation according to the following expression can be used to calculate a volume based on a voice signal.

$$\text{Speech volume}=m*\text{Peak level}+n*\text{Average level}$$

where m and n are coefficients representing a mixture ratio of the peak level and the average level. The peak level is the maximum value of a voice signal in the period from the start position of speech to the end position of speech of the trainee and the average level is the average value of valid data (voice signal in the period from time t2 to time t3 and the period from time t4 to time t5 in FIG. 7B) in this period. Generally, for example, it is likely that the speech level of the trainee is large at the beginning and gradually reduces. Accordingly, "efforts" at the beginning can be difficult to evaluate when using only the average level. Therefore, the peak level can be digitized and added as "efforts".

In accordance with an exemplary embodiment, the average value can be calculated as an arithmetic average, root mean square, or the like. When training text is associated with voice signal waveforms, a weighted average can be used that more highly evaluates the start point of a phoneme.

Since the ratio of m and n depends on the calculation method of the average level or the characteristics of the entire system such as the microphone sensitivity or the like, an appropriate value needs to be determined according to the system. In the embodiment, when the average level was calculated using an arithmetic average, the ratio was determined to be 1:4 based on sensory evaluation.

Figure 6A:
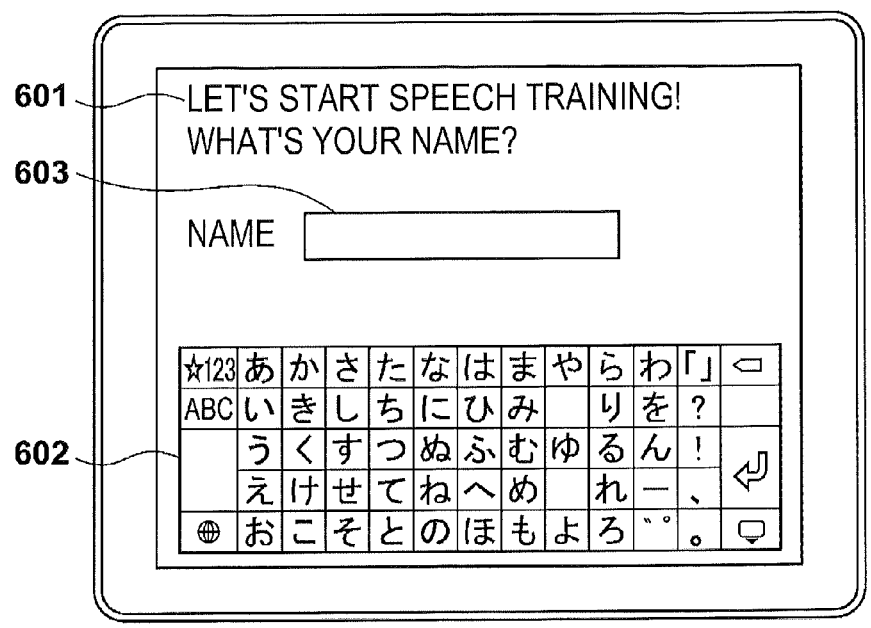
FIG. 6A shows display on a tablet terminal in the speech training process.

Upon calculating the speech volume as described above, the processing proceeds to step S412. In step S412, the controller 201 functions as comparison result reporting means for reporting a result of comparison between the calculated volume and the volume predetermined as a target volume. In accordance with an exemplary embodiment, for example, the controller 201 can evaluate this speech by comparing the speech volume calculated in step S411 with the target speech volume and, in step S413, can present the comparison result. The evaluation may be presented by a voice via the voice output unit 213 and the speaker 122 as shown in step S507 or by display on the tablet terminal 150 as shown by reference numeral 631 in FIG. 6D.

The evaluation displayed as an evaluation statement 632 or reported by a voice (S507) is shown below when, for example, the measured speech volume is N and the target speech volume is R. However, it will be appreciated that the following evaluation is only an example and the evaluation is not limited to this example.

N−R≥0: "VOLUME IS APPROPRIATE."
N−R<0: "VOLUME IS TOO SMALL. SPEAK LOUDLY."

In step S414, the controller 201 associates the voice signal recorded in the memory unit 202 in step S410, the speech volume obtained in step S411, and the evaluation result in step S412 (such as, for example, the (N−R) value above, evaluation statement to be displayed, or the like) with the ID of the exercised training text item and records them as the exercise situation 324. In this way, the corresponding exercise situations 324 in the trainee information table 223 are updated. In recording of the voice signal, the time period (the time period in which speech is actually recorded) from time t2 to time t5 in FIG. 7B may be extracted and recorded. When using the (N−R) value as the evaluation result, this value may be used as the above evaluation value indicating the degree of evaluation.

Subsequently, in step S415, the controller 201 presents a menu 633 (FIG. 6D) using the tablet terminal 150. For example, the following items can be displayed in the menu 633. The menu 633 may be displayed on the touch panel display 121 as an operation performed by the speech therapist.

[PLAY SPEECH]: Plays the recorded speech using the speaker 122.
[AGAIN]: Performs speech exercise again using the previous training text item.
[NEXT TEXT]: Performs speech exercise using a new training text item.
[CHANGE LEVEL]: Changes the level and performs speech exercise using a new training text item.
[FINISH TRAINING]: Finishes the speech training.

When [PLAY SPEECH] is selected in step S416, the processing proceeds to step S417 and the recorded speech is played. The exercise situation 324 records a predetermined number of past speeches and the user (speech therapist or trainee) can select and play a desired speech. For example, FIG. 3B shows two pieces (#1 and #2) of past recording data. In this case, when [PLAY SPEECH] is selected, the controller 201 causes the user (speech therapist or trainee) to specify the record (last, last but one, or the like) to be played. This specification may be received by a voice or may be received by an operation input from the tablet terminal 150 or the touch panel display 121. Then, the controller 201 reads the voice data of the specified record from the storage unit 203 and makes control so that the voice output unit 213 performs a voice output according to the voice data.

When [AGAIN] is selected in step S416, the processing proceeds to step S409, the controller 201 presents the training text item currently selected, and the above processing is repeated. When [NEXT TEXT] is selected in step S416, the processing proceeds to step S408, the controller 201 obtains, from the text database 222, a new training text item with the level currently selected, and performs the processing in step S409 and later using the new training text item.

Figure 5:
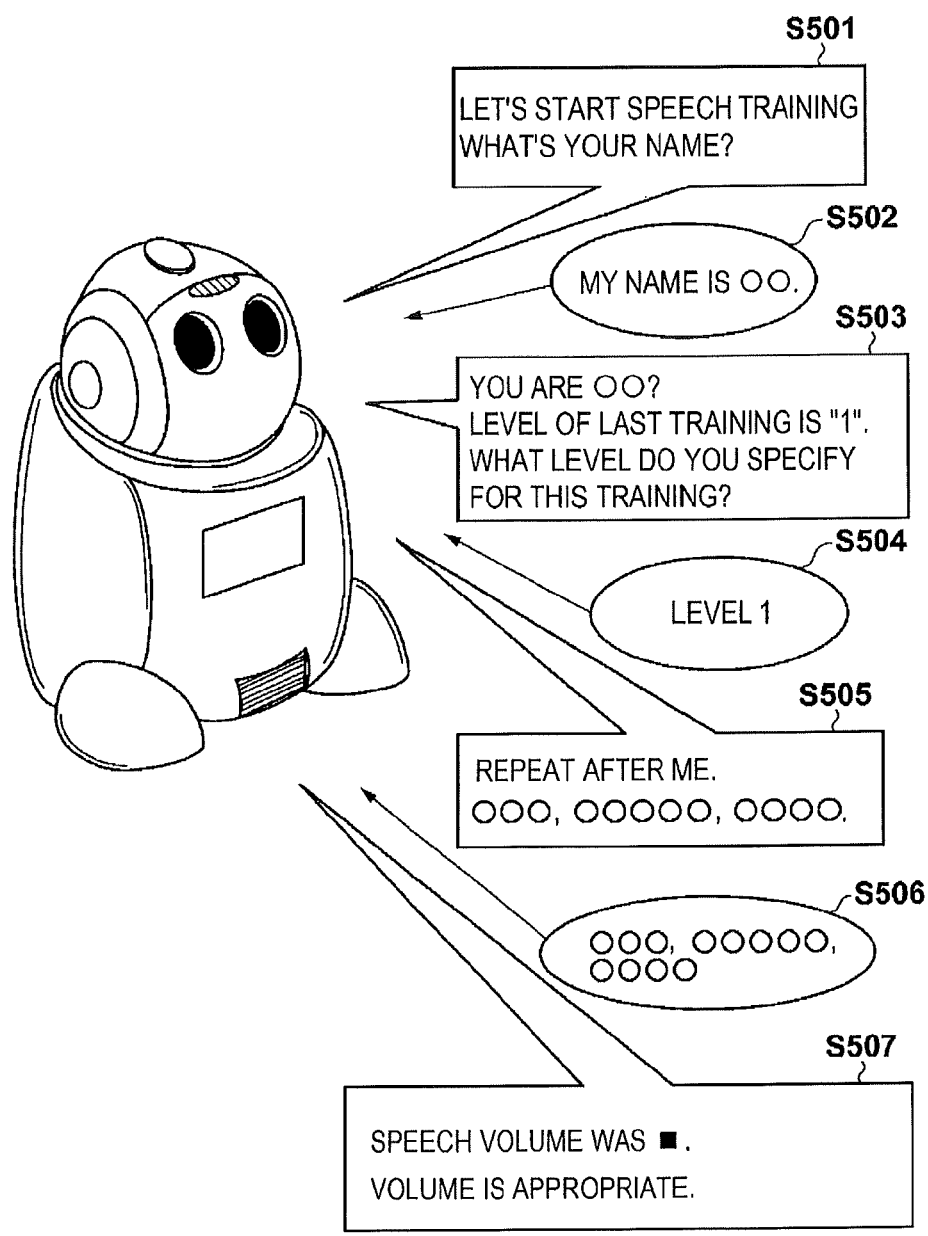
FIG. 5 shows interactions with a trainee in the speech training process.
Figure 6B:
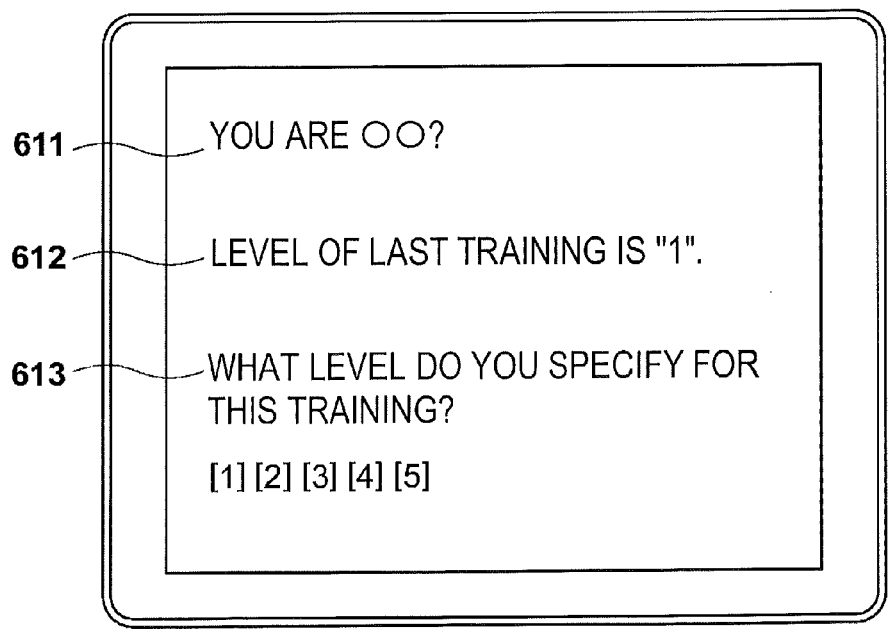
FIG. 6B shows display on the tablet terminal in the speech training process.
Figure 6C:
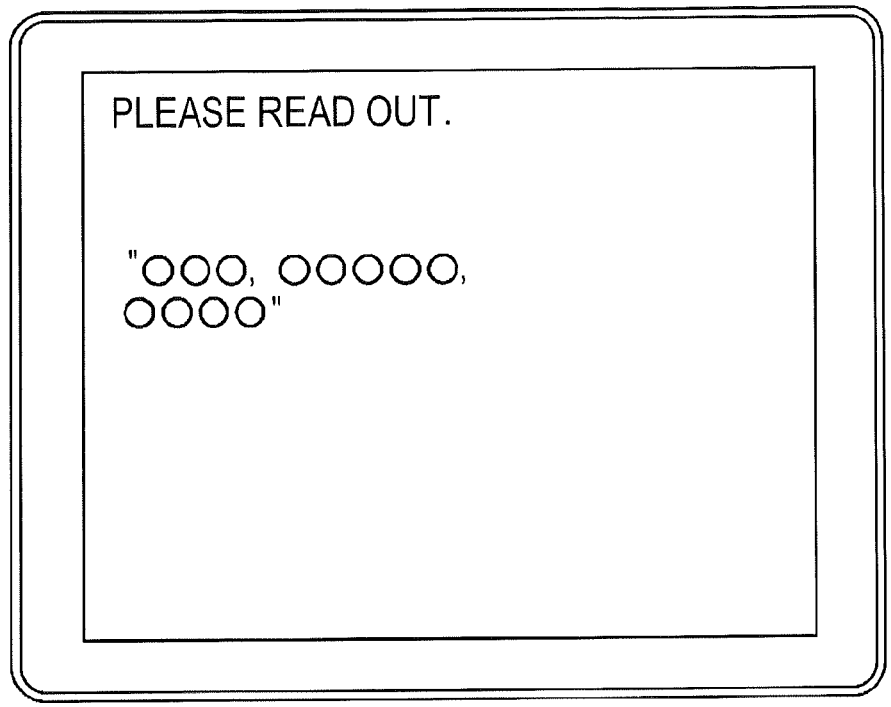
FIG. 6C shows display on the tablet terminal in the speech training process.
Figure 6D:
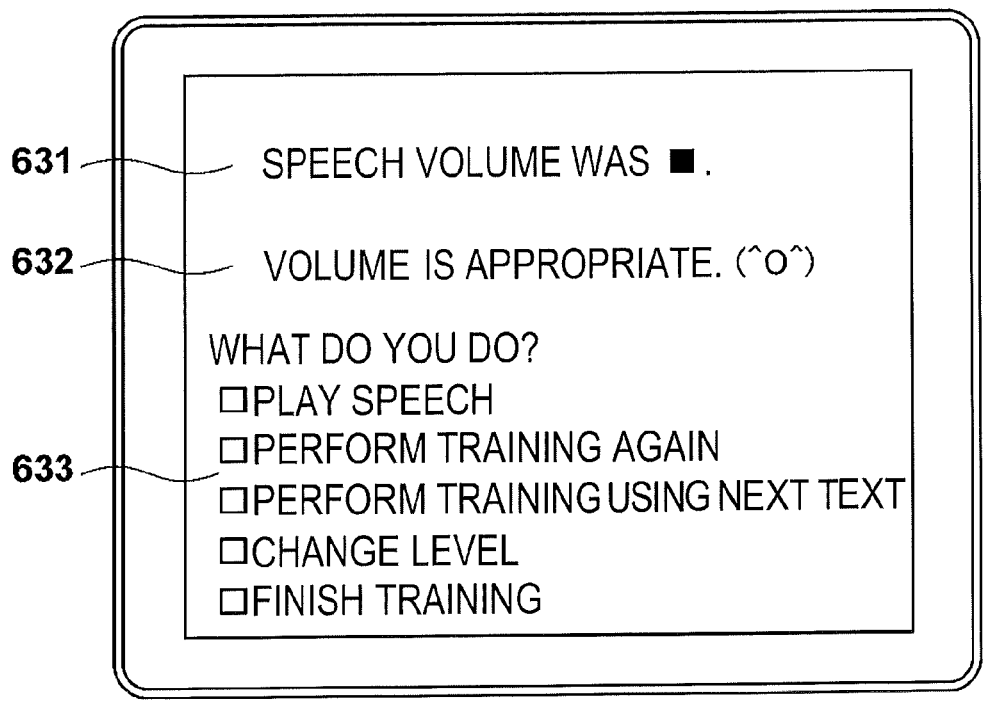
FIG. 6D shows display on the tablet terminal in the speech training process.

When [CHANGE LEVEL] is selected in step S416, the processing proceeds to step S407, performs the voice output shown in the step S503 in FIG. 5 or the display shown in FIG. 6B, and waits for a new training level to be input. When a new training level is input, the processing in step S408 and later is performed. When [FINISH TRAINING] is selected in step S416, the processing ends.

As described above, according to the embodiment, the trainee can perform speech exercise while interacting with the rehabilitation robot 100 using a voice or an operation input from a tablet terminal. In addition, since the speech volume and evaluation result are reported each time the trainee speaks, the trainee can perform exercise while checking the performance of speech.

Although the training text item to be obtained is selected from the text database 222 depending on the specified level (regardless of the trainee) in the above embodiment, the invention is not limited to this embodiment. For example, the speech therapist may specify a training text item with any level depending on the situation of the trainee. For example, the speech therapist may select a training text item to be used by the trainee from the text database 222 using an external apparatus connected to the rehabilitation robot 100 and registers the training text item in the trainee information table 223. In accordance with an exemplary embodiment, for example, as shown in FIG. 8A, the trainee information table 223 is provided with level fields 801 each including the ID of a training text item used for each level, for each trainee. The speech therapist can register a desired training text item in the text database 222 in a desired level using the external apparatus. In this way, training text items corresponding to each level in the trainee information table 223 are registered using their IDs. In step S408, the controller 201 selects the training text item to be presented by selecting one of registered IDs with the level specified in step S407 with reference to the level field 801 of the trainee information table 223.

As described above, in the first embodiment, the rehabilitation robot 100 presents a text item appropriate for speech training to the trainee and evaluates the speech state of the trainee, so speech training can be performed correctly only by the trainee.

Second Embodiment

Dysarthric patients with language deficits may have difficulties in pronouncing specific sounds such as "TA", "KA-row", and the like. The second embodiment considers the inclusion of such sounds (referred to below as weak sounds) difficult for the trainee to pronounce when selecting a training text item. Intentional selection of a training text item including a weak sound for speech training can achieve speech training for improving the speech volume and overcoming the weak sound. The structure of the information processing apparatus according to the second embodiment is similar to that of the first embodiment.

FIG. 8B shows the trainee information table 223 in which a weak sound 802 difficult for the trainee to pronounce can be registered. The speech therapist identifies the sounds difficult for the trainee to pronounce and registers the results in the weak sound 802 of the trainee information table 223 shown in FIG. 8B. Since the sounds difficult to pronounce depend on the trainee, the field of the weak sound 802 can be provided for each trainee.

The speech training process according to the second embodiment is substantially the same as in the first embodiment except that a weak sound is used as one of selection conditions when a training text item is selected. In accordance with an exemplary embodiment, for example, when the controller 201 selects a training text item with a specified level from the text database 222 in step S407 in FIG. 4, the controller 201 searches for a training text item with a weak sound. Accordingly, the training text item used for speech training can include a weak sound difficult for the trainee to pronounce, so the trainee can exercise speech training for the weak sound at the same time.

The method for selecting a training text item is not limited to the above. For example, a training text item including a weak sound may not necessarily be selected for each time and the training text may be selected only once per a predetermined number of times. Alternatively, the number of weak sounds included in one training text item may be used as a selection condition by associating the number with the training level. For example, control may be performed so that a training text item including one weak sound is selected for training level 1 and a training text item including two weak sounds is selected for training level 2. Alternatively, when the number of weak sounds included in a training text item is equal to or more than a predetermined number, the training text item may have a level one higher than the level set in the text database 222.

As described above, since a training text item including a sound difficult for a patient with language deficits to pronounce is actively selected in speech training according to the second embodiment, training for speech volume and training for pronouncing a weak sound can be performed concurrently. In addition, by comparing the speech volume between a training text item including a weak sound and a training text item not including the weak sound, the effect or the like of the weak sound on the speech volume can be determined, thereby providing the speech therapist with auxiliary information necessary to create a rehabilitation plan.

Third Embodiment

The first embodiment describes the structure in which the trainee speaks a selected training text item and the speech volume is calculated to make evaluation. The second embodiment describes the structure in which a training text item is selected by specifying the presence or absence of a weak sound of the trainee as a selection condition. The third embodiment will describe the structure in which training for uttering a weak sound correctly is taken into consideration.

Generally, for example, the waveforms of one sound at the beginning and one sound at the end of a voice signal can be easily clipped and voice recognition can be performed at high precision. For example, when "a-me-ga-fu-ru" is input by a voice, whether the sound "a" at the beginning and the sound "ru" at the end are pronounced correctly can be determined at relatively high precision. In the speech training process in the third embodiment, training for weak sounds is provided using such features of voice recognition technology.

Figure 9:
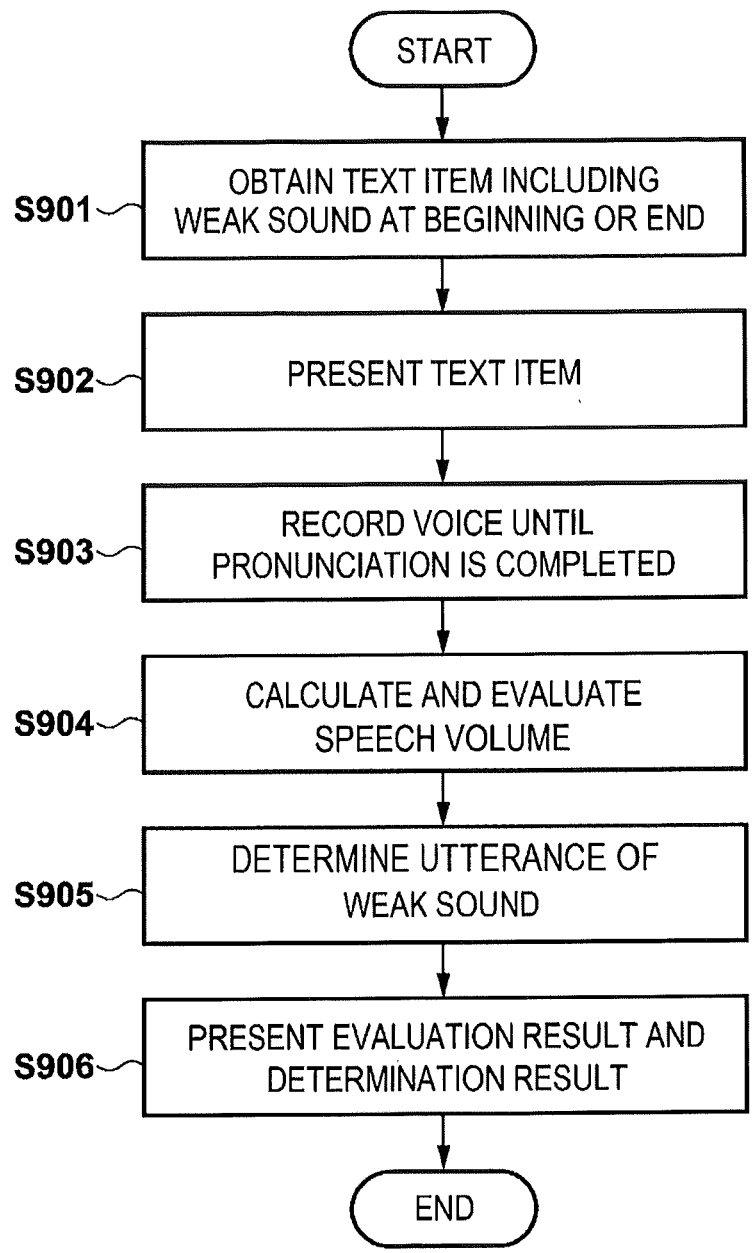
FIG. 9 is a flowchart showing the evaluation of the pronunciation of a weak sound.

FIG. 9 is a flowchart showing a speech training process according to the third embodiment, which replaces steps S408 to S413 of the speech training process (FIG. 4) in the first embodiment. In step S901, the controller 201 obtains a weak sound of the trainee from the trainee information table 223 and obtains a training text item including the weak sound at the beginning or the end from the text database 222. In step S902, the controller 201 presents the training text item obtained in step S901 by a voice output or character display. The text item is presented as shown in step S409.

After presenting the training text item in step S902, the controller 201 starts recording the speech of the trainee in step S903. The recorded data is held in the memory unit 202.

Then, in step S904, the controller 201 calculates the speech volume by analyzing the recorded data and evaluates the speech by comparing the calculated speech volume with a predetermined target speech volume. The above processing from step S902 to step S904 is similar to that from step S409 to step S411.

In step S905, the controller 201 determines whether the one sound at the beginning or the one sound of the end of the training text item presented in step S902 is spoken correctly. Since a determination can be made as to whether a weak sound is pronounced correctly, the following determinations can be made.

When the training text item including the weak sound at the beginning is presented in steps S901 and S902, a determination can be made as to whether the one sound at the beginning is pronounced correctly.

When the training text item including the weak sound at the end is presented in steps S901 and S902, a determination can be made as to whether the one sound at the end is pronounced correctly.

When the training text item including the weak sound at the beginning and the end is presented in steps S901 and S902, a determination can be made as to whether each of the one sound at the beginning and the end is pronounced correctly.

In step S906, the evaluation result in step S904 and the determination result in step S905 are presented. The evaluation result in step S904 is presented as described in the first embodiment. In the presentation of the determination result in step S905, the trainee is notified of whether the weak sound has been determined correctly. Whether the weak sound is pronounced correctly can be determined by, for example, matching between the waveform of a voice signal recorded in step S903 and the reference waveform. Accordingly, the degree of matching may be classified into a plurality of levels and the determination result may be presented depending on the level to which the degree of matching obtained by matching belongs. For example, the degree of matching can be classified into three levels in the descending order of the degree and the messages as shown below are displayed depending on the level.

Level 3: Weak sound "O" has been pronounced almost correctly.
Level 2: Weak sound "O" has been pronounced at barely audible levels.
Level 1: Please practice the pronunciation of weak sound "O".

As described above, in the third embodiment, speech training is performed using a training text item including a weak sound at the beginning or the end and whether the weak sound has been correctly pronounced is reported. Accordingly, the trainee can exercise training while grasping the effects of the training for the weak sound.

Although training for pronouncing weak sounds is exercised together with training for speech volume in the above third embodiment, only training for pronouncing weak sounds may be performed. Although a training text item including a weak sound at the beginning, the end, or both the beginning and the end is selected in the above embodiment, training may be performed by separating between training text items including a weak sound at the beginning, the end, and both the beginning and the end. In accordance with an exemplary embodiment, this can detect a symptom in which, for example, a training text item including a weak sound at the beginning cannot be pronounced well, but a training text item including a weak sound at the end can be pronounced.

Fourth Embodiment

Figure 10:
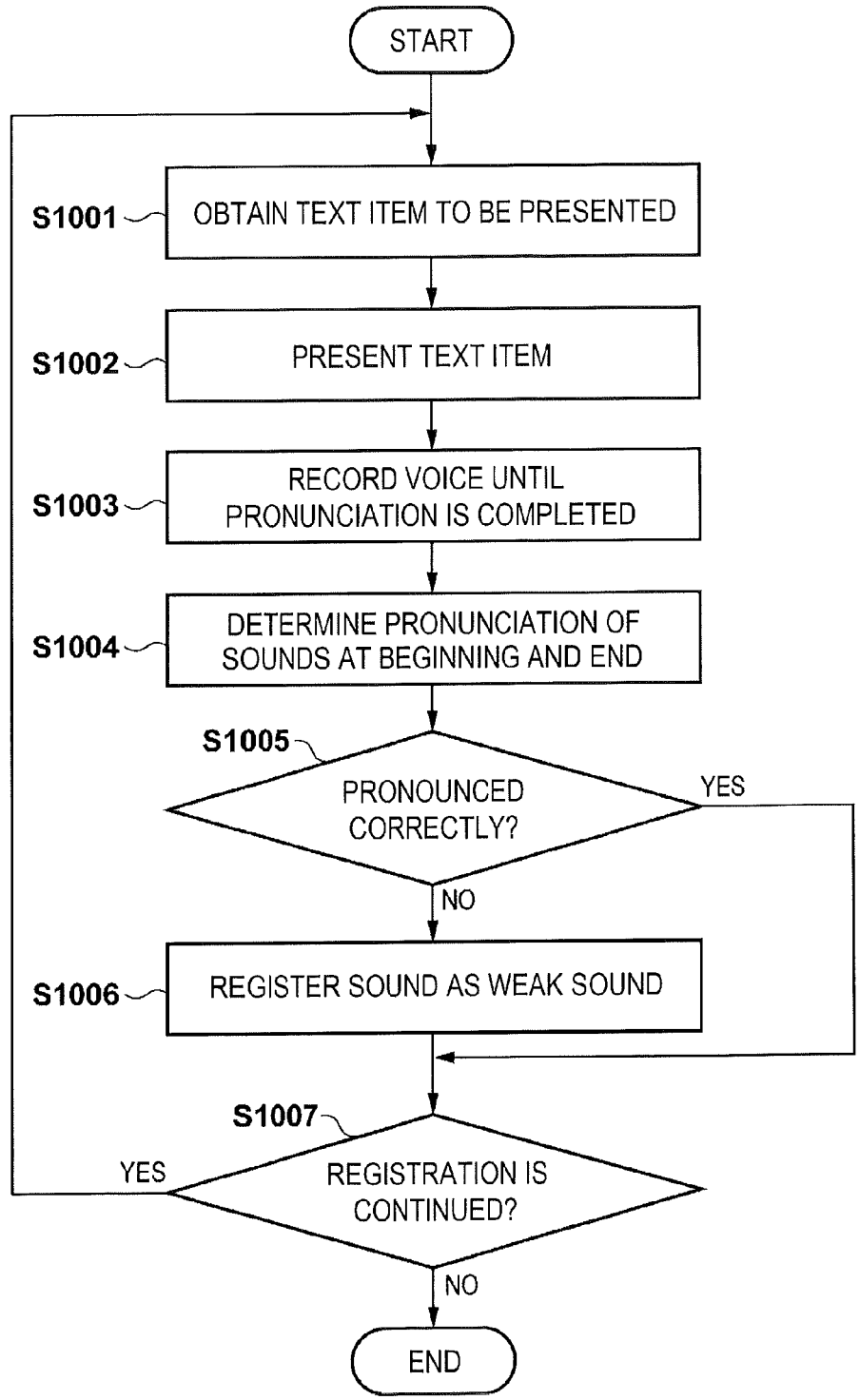
FIG. 10 is a flowchart showing the automatic collection of weak sounds.

The weak sounds of the trainee are registered by the speech therapist in the second and third embodiments, but the weak sounds are registered automatically in the fourth embodiment. FIG. 10 shows a weak sound registration process according to the fourth embodiment.

In step S1001, the controller 201 obtains a training text item from the text database 222. In step S1002, the controller 201 presents the obtained training text item to the trainee and, in step S1003, records the speech. Such processing is similar to that from steps S408 to S410 in the first embodiment (FIG. 4).

In step S1004, the controller 201 determines whether the voice recognition results of one sound at the beginning and one sound at the end of the voice signal of the recorded speech match the sounds that should be pronounced at the beginning and the end of the presented training text item. This matching process is similar to that described in the third embodiment (step S905). As a result of the determination, when the sound is determined to be pronounced correctly (match), the processing proceeds to step S1007. When the sound is determined to be pronounced incorrectly (mismatch), the processing proceeds to step S1006 and the controller 201 functions as registration means and registers the sound determined to be pronounced incorrectly in the trainee information table 223 as a weak sound. In step S1007, the processing returns to step S1001 to continue the registration process until an end instruction is received.

In the registration process in the fourth embodiment, weak sounds of the trainee are registered automatically, thereby assisting the speech therapist more strongly.

In step S1006, the sound pronounced at a predetermined level or lower can be registered a predetermined number of times instead of immediately registering the sound determined to be pronounced incorrectly. For example, the word that was determined to be level 1 more than a predetermined number of times in the level determination may be registered. In this case, a weak sound can be obtained more efficiently if the training text item to be obtained in step S1001 does not include the sound determined to be pronounced correctly in step S1005 at the beginning or the end and includes the sound determined to be pronounced incorrectly in step S1005 at the beginning or the end.

Although the text database 222 and the trainee information table 223 are included in the information processing apparatus in the above embodiments, the invention is not limited to the embodiments. For example, it is appreciated that the text database 222 and the trainee information table 223 may be stored in an external server and required information may be obtained via wireless communication, wired communication, the Internet, or the like.

The invention is not limited to the above embodiments and various changes and modifications can be made without departing from the spirit and scope of the invention. Accordingly, the following claims are appended to publicize the scope of the invention.

The detailed description above describes information processing apparatus and an information processing method. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An information processing apparatus for utterance training in speech rehabilitation, the information processing apparatus comprising:
a microphone configured to capture utterances by a trainee as a digitized voice signal;
a speaker configured to output a synthesized voice to the trainee in response to the captured utterances;
a display configured to display text data to the trainee in response to the captured utterances; and
a processor configured to:
generate a report about content to be uttered in the utterance training to the trainee of the utterance training;
calculate a volume of the digitized voice signal uttered by the trainee in response to the report;
compare the volume calculated and a volume predetermined as a target volume; and
change output information related to an evaluation of the volume of the digitized voice signal uttered by the trainee to the trainee based on whether or not the calculated volume is less than the volume predetermined as the target volume, and wherein the output information is presented to the trainee via the speaker or the display, wherein the calculated volume of the digitized voice signal uttered by the trainee is equal to m times peak level plus n times average level, wherein m and n are coefficients representing a ratio of the peak level to the average level, the peak level being a maximum value of the digitized voice signal in a period from a start position to an end position of the speech of the trainee and the average level is an average value of the digitized voice signal.

2. The information processing apparatus according to claim 1, comprising:
a memory configured to:
store a plurality of text items for the utterance training including a word, a word string, or a sentence,
select one of the plurality of text items stored in the memory, and
report the selected text item to the trainee as the content.

3. The information processing apparatus according to claim 2, wherein the processor is configured to:
register a weak sound difficult for the trainee to pronounce, the weak sound being a pronunciation of a text item, which is difficult for the trainee to pronounce; and
select one text item including the weak sound from the plurality of text items stored in the memory and report the selected text item to the trainee as the content.

4. The information processing apparatus according to claim 3, wherein the processor is configured to:
select one text item including the weak sound at a beginning or an end from the plurality of text items stored in the memory and report the selected text item to the trainee as the content.

5. The information processing apparatus according to claim 3, wherein the processor is configured to:
select one text item including a number of weak sounds, the number corresponding to a specification level specified as a level of utterance training, from the plurality of text items stored in the memory and report the selected text item to the trainee as the content.

6. The information processing apparatus according to claim 3, wherein the processor is configured to:
determine whether a voice recognition result of one sound at a beginning of the digitized voice signal uttered by the trainee in response to the report matches a word at a beginning of the text item and, if the voice recognition result does not match the word at the beginning, registers the word at the beginning as the weak sound; and
determine whether a voice recognition result of one sound at an end of the digitized voice signal uttered by the trainee in response to the report matches a word at an end of the text item reported and, if the voice recognition result does not match the word at the end, registers the word at the end as the weak sound.

7. The information processing apparatus according to claim 4, wherein the processor is configured to:
determine whether a voice recognition result of one sound at a beginning of the digitized voice signal uttered by the trainee in response to the report matches a word at a beginning of the text item and, if the voice recognition result does not match the word at the beginning, registers the word at the beginning as the weak sound and
determine whether a voice recognition result of one sound at an end of the digitized voice signal uttered by the trainee in response to the report matches a word at an end of the text item and, if the voice recognition result does not match the word at the end, registers the word at the end as the weak sound.

8. The information processing apparatus according to claim 1, comprising:
the speaker for outputting the synthesized voice or the display for displaying the text data on a screen, and wherein the speaker or the display outputs the content to the trainee.

9. The information processing apparatus according to claim 1, comprising:
the speaker for outputting the synthesized voice or the display for displaying the text data on a screen, and wherein the speaker or the display outputs the result of the comparison.

10. An information processing method performed by an information processing apparatus for utterance training in speech rehabilitation, the information processing apparatus including a microphone configured to capture utterances by a trainee as a digitized voice signal, a speaker configured to output a synthesized voice to the trainee in response to the captured utterances, a display configured to display text data to the trainee in response to the captured utterances, and a processor configured to execute the method comprising:
generating a report about content to be uttered in the utterance training to the trainee of the utterance training;
receiving the digitized voice signal uttered by the trainee in response to the report on the information processing apparatus via the microphone;
calculating a volume of the digitized voice signal uttered by the trainee in response to the report;
comparing the volume calculated and a volume predetermined as a target volume; and
changing output information related to an evaluation of the volume of the digitized voice signal uttered by the trainee to the trainee based on whether or not the calculated volume is less than the volume predetermined as the target volume, and wherein the output information is presented to the trainee via the speaker or the display, wherein the calculated volume of the digitized voice signal uttered by the trainee is equal to m times peak level plus n times average level, wherein m and n are coefficients representing a ratio of the peak level to the average level, the peak level being a maximum value of the digitized voice signal in a period from a start position to an end position of the speech of the trainee and the average level is an average value of the digitized voice signal.

11. A non-transitory computer-readable recording medium with a program stored therein which causes a computer to function as an information processing apparatus, the information processing apparatus including a microphone configured to capture utterances by a trainee as a digitized voice signal, a speaker configured to output a synthesized voice to the trainee in response to the captured utterances, a display configured to display text data to the trainee in response to the captured utterances, the computer-readable recording medium configured to execute a process comprising:

generating a report about content to be uttered in the utterance training to the trainee of the utterance training;

receiving the digitized voice signal uttered by the trainee in response to the report on the information processing apparatus via the microphone;

calculating a volume of the digitized voice signal uttered by the trainee in response to the report;

comparing the volume calculated and a volume predetermined as a target volume; and changing output information related to an evaluation of the volume of the digitized voice signal uttered by the trainee to the trainee based on whether or not the calculated volume is less than the volume predetermined as the target volume, and wherein the output information is presented to the trainee via the speaker or the display, wherein the calculated volume of the digitized voice signal uttered by the trainee is equal to m times peak level plus n times average level, wherein m and n are coefficients representing a ratio of the peak level to the average level, the peak level being a maximum value of the digitized voice signal in a period from a start position to an end position of the speech of the trainee and the average level is an average value of the digitized voice signal.

12. The computer-readable recording medium according to claim 11, comprising:

storing a plurality of text items for the utterance training including a word, a word string, or a sentence;

selecting one of the plurality of text items; and reporting the selected text item to the trainee as the content.

13. The computer-readable recording medium according to claim 12, further comprising:

registering a weak sound difficult for the trainee to pronounce, the weak sound being a pronunciation of a text item, which is difficult for the trainee to pronounce;

selecting one text item including the weak sound from the plurality of text items; and reporting the selected text item to the trainee as the content.

14. The computer-readable recording medium according to claim 13, comprising:

selecting one text item including the weak sound at a beginning or an end from the plurality of text items; and reporting the selected text item to the trainee as the content.

15. The computer-readable recording medium according to claim 13, comprising:

selecting one text item including a number of weak sounds, the number corresponding to a specification level specified as a level of utterance training, from the plurality of text items; and reporting the selected text item to the trainee as the content.

16. The computer-readable recording medium according to claim 13, comprising:

determining whether a voice recognition result of one sound at a beginning of the digitized voice signal uttered by the trainee in response to the report matches a word at a beginning of the text item reported and, if the voice recognition result does not match the word at the beginning, registering the word at the beginning as the weak sound; and determining whether a voice recognition result of one sound at an end of the digitized voice signal uttered by the trainee in response to the report matches a word at an end of the text item reported and, if the voice recognition result does not match the word at the end, registering the word at the end as the weak sound.

17. The computer-readable recording medium according to claim 14, comprising:

determining whether a voice recognition result of one sound at a beginning of the digitized voice signal uttered by the trainee in response to the report matches a word at a beginning of the text item reported and, if the voice recognition result does not match the word at the beginning, registering the word at the beginning as the weak sound; and determining whether a voice recognition result of one sound at an end of the digitized voice signal uttered by the trainee in response to the report matches a word at an end of the text item reported and, if the voice recognition result does not match the word at the end, registering the word at the end as the weak sound.

18. The computer-readable recording medium according to claim 11, comprising:

reporting the content to the trainee using the speaker or the display.

19. The computer-readable recording medium according to claim 11, comprising:

reporting the result of comparison using the speaker or the display.

20. The information processing apparatus according to claim 3, wherein the processor is configured to:

register at least one weak sound for each trainee, the at least one weak sound being a pronunciation of a text item, which is difficult for each trainee to pronounce.

* * * * *